United States Patent [19]

Dutta et al.

[11] Patent Number: 5,167,982
[45] Date of Patent: Dec. 1, 1992

[54] METHOD OF DETECTING A DEGRADED PHOSPHOR IN A LAMP PHOSPHOR SUSPENSION

[75] Inventors: Arunava Dutta, Chestnut Hill; Ernest A. Dale, Hamilton; Leonard V. Dullea, Peabody, all of Mass.

[73] Assignee: GTE Products Corporation, Danvers, Mass.

[21] Appl. No.: 632,460

[22] Filed: Dec. 21, 1990

[51] Int. Cl.$^5$ .......................... B05D 5/12; B05D 5/06
[52] U.S. Cl. .................................. 427/8; 427/67; 427/68; 427/595; 313/485
[58] Field of Search .............. 427/64, 67, 68, 54.1, 427/8; 313/485

[56] References Cited

U.S. PATENT DOCUMENTS

| | | | |
|---|---|---|---|
| 3,833,398 | 9/1974 | Schreurs | 427/67 |
| 3,999,993 | 12/1976 | Patel et al. | 427/68 |
| 4,121,132 | 10/1978 | Repsher | 313/486 |
| 4,148,935 | 4/1979 | Schreurs | 427/67 |
| 4,219,587 | 8/1980 | Oba et al. | 427/64 |
| 4,803,400 | 2/1989 | Peters et al. | 313/489 |

OTHER PUBLICATIONS

Kotrly and Sucho, Handbook of Chemical Equilibria in Analytical Chemistry, Ellis Horwood, 1985.

*Primary Examiner*—Shrive Beck
*Assistant Examiner*—Roy V. King
*Attorney, Agent, or Firm*—Robert E. Walter

[57] ABSTRACT

A an europium doped yttrium oxide red phosphor in a water base phosphor coating suspension is checked for degraded phosphor by (a) centrifuging the suspension, (b) separating an aqueous portion from a solids portion, (c) exposing a surface portion of said solids to UV radiation at 254 nm or 365 nm, (d) observing the presence or absence of fluorescence from said top layer of solids wherein the absence of fluorescence is indicative of a degraded phosphor.

1 Claim, 4 Drawing Sheets

METHOD OF DETECTING A DEGRADED PHOSPHOR IN A LAMP PHOSPHOR SUSPENSION

TECHNICAL FIELD OF THE INVENTION

This invention relates to phosphors and more particularly to water base suspensions of phosphors.

BACKGROUND OF THE INVENTION

In fabrication of fluorescent lamps, a phosphor layer is applied to the interior surface of a glass envelope using a water base or organic base paint-like suspension of phosphor powder. Environmental considerations favor the use of an aqueous (water base) suspension. The phosphor layer may be applied directly to the glass or may alternatively be applied to a previously applied coating of, for example, phosphor or reflective material.

Although the composition of the phosphor coating suspension may vary from lamp manufacturer to lamp manufacturer, the suspension usually includes, in addition to the phosphor, a film forming binder, solvent(s) for the binder, and, if necessary, surfactants, defoamers, and wetting agents. The coating suspension may further include submicron particle size alumina, e.g., Aluminum Oxide C (ALON C), manufactured by Degussa, Inc.

In triphosphor coating suspensions, an ALON C content of 2 to 10% weight percent of the suspension is typical.

Many of the non-phosphor components of the coating suspension interfere with efficient lamp operation and longevity, and are therefore removed from the phosphor coating during the manufacturing process by high temperature air oxidation in a manufacturing step known in the art as "lehring."

The submicron particle size alumina is not removed during the lehring step. The submicron particle size alumina assists in the formation of a uniform adherent phosphor layer on the lamp surface.

Butler, in his book, *Fluorescent Lamp Phosphors, Technology and Theory,* Penn State University Press (1980), describes lamp coating technology and its evolution from the nitrocellulose and ethylcellulose-type lacquers to the newer polymeric binders used with water base suspension systems.

Depending upon the chemical composition of the phosphor and method of preparation, phosphors may exhibit some differences in performance depending upon whether a water base or organic base suspension is used to apply the phosphor coating to the bulb. Usually these differences are not significant unless the phosphor has a tendency to react chemically with one of the suspension components.

SUMMARY OF THE INVENTION

A method has been found which reduces substantially the degradation of the red phosphor, $Y_2O_3$:Eu, in water base fluorescent lamp suspensions, thereby prolonging the shelf life of suspensions containing $Y_2O_3$:Eu phosphor. An example is a suspension which contains red, blue, and green phosphors, commonly referred to in the art as a triphosphor suspension. The degradation of the red component of phosphor suspensions is due to phosphor solubility and/or crystallite breakup in an aqueous medium.

The method of the invention maintains the integrity of a water base phosphor coating suspension including europium doped yttrium oxide phosphor and alumina.

The method of the invention comprises controlling the pH of a water base phosphor coating suspension including europium doped yttrium phosphor and alumina from 9 to 9.5.

For a better understanding of the present invention, together with other and further advantages and capabilities thereof, reference is made to the following disclosure and appended claims in connection with the above-described drawings.

DETAILED DESCRIPTION OF THE INVENTION

As discussed above, it has been found that the red-emitting phosphor $Y_2O_3$:Eu undergoes degradation in a water base phosphor coating suspension system.

The degradation is caused by dissolution of the europium activated yttrium oxide phosphor in the water base suspension system and/or breakup of the phosphor into crystallites (smaller size particles).

A typical composition of a triphosphor blend is as follows: 18.2 kg red phosphor; 9.4 kg green phosphor; 1.9 kg blue phosphor; 37 liters water; 2.95 kg ALON C; 0.3 kg polyox; 3.1 cc defoamer (Hercules type 831) and 1.3 cc surfactant (BASF 25R-1).

Preferably the water soluble binder is poly(ethylene oxide), also referred to as POLYOX as made by Union Carbide.

Phosphor solubility leads to transport of yttrium (and europium) in the form of various ions, from the phosphor to the liquid phase. It has been found that the extent of this solubility increases dramatically as the pH of the triphosphor suspension decreases.

The decrease in pH is due to the need for the addition of certain necessary components, like ALON C, to the mix.

ALON C behaves as an acid during the initial stage of its dispersion in a water base suspension. Addition of 3 grams of the ALON C to 100 cc of water at an initial pH of 7, drops the pH very rapidly to 5.1 Addition of silver nitrate to the suspension liquid phase, after centrifugation, yields a white precipitate indicating the presence of chloride ions in the liquid. The acidity is possibly due to the presence of one or more of the following species on the surface and/or in the bulk: aluminum chloride, aluminum oxychloride, etc. The first named material, i.e., aluminum chloride, is used in the manufacture of ALON C. chemical analysis on a typical lot of ALON C reveals about 100 ppm Cl in the material.

Figure 1:
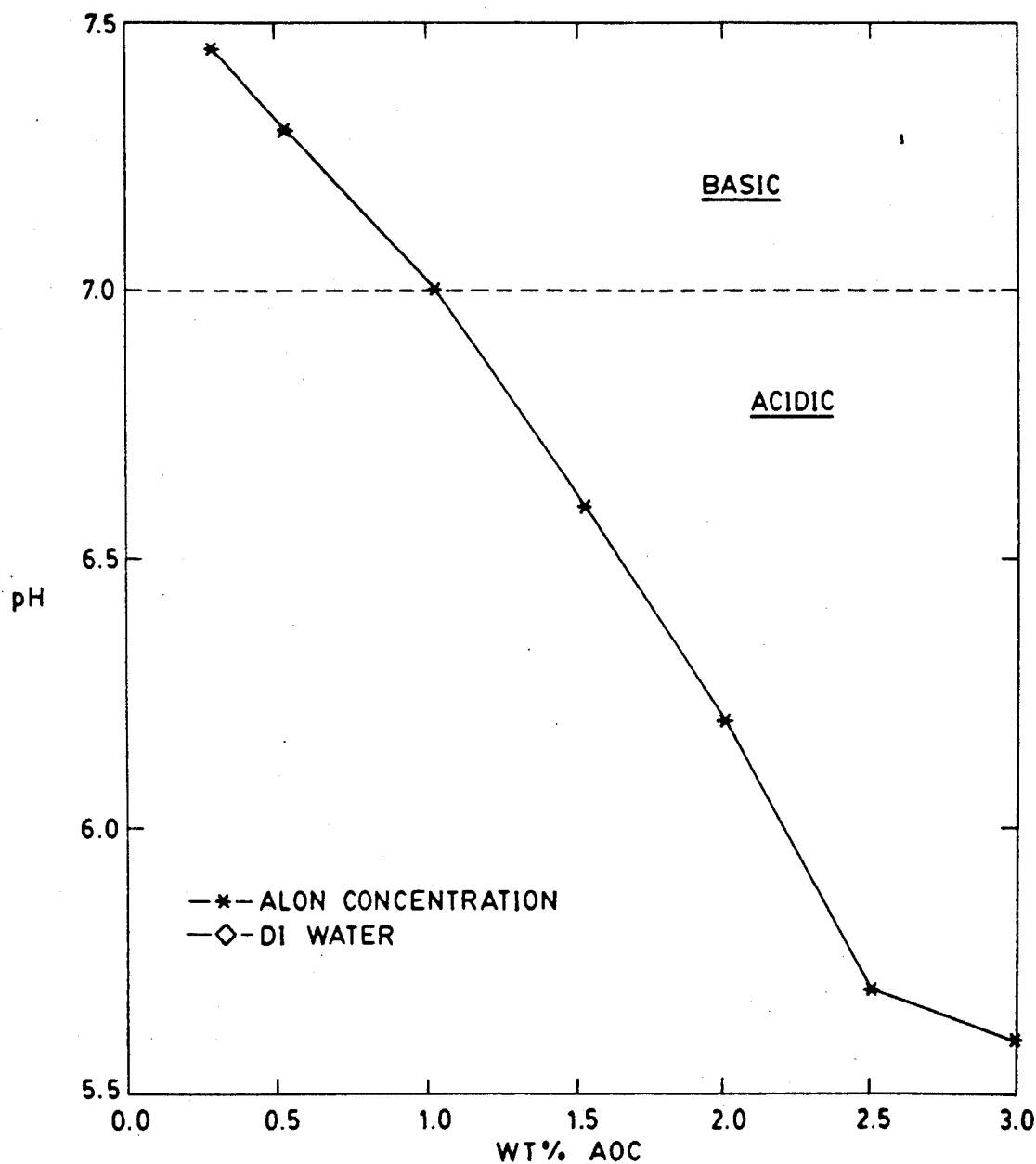
FIG. 1 graphically illustrates pH of a suspension of ALON C in deionized water as a function of the weight % of the ALON C in the suspension after 1,250 hours hold over.

As graphically represented in FIG. 1, the magnitude of pH drop for a solution of deionized water and ALON C is a strong function of the concentration of the ALON C in the solution.

Subsequent rise of the suspension pH, due to the inherent basic nature of yttrium oxide, leads to precipitation of various ions of yttrium (and europium) in the form of a scum on the surface of the phosphor particles. In addition to creating dispersion problems, this scum also causes an unacceptable loss in lumens due to lamp lehring problems.

Dissolution of europium-doped yttrium oxide causes further concerns when it is used as a component of a blend including two or more different phosphors.

For example, as discussed earlier, a triphosphor blend is a mixture of a red phosphor, a green phosphor, and a blue phosphor formulated to produce white light when used in a fluorescent lamp.

Phosphor blends including two phosphors, e.g., $Y_2O_3$:Eu and another phosphor, are also used in fluorescent lamps.

When the red europium doped yttrium oxide phosphor component of a triphosphor blend dissolves in the coating suspension, the formulation of the blend is changed, thus requiring additional amounts of the red phosphor to be added to the suspension to replace the red phosphor that has dissolved and correct the color imbalance caused by such dissolution.

Furthermore, the red $Y_2O_3$:Eu phosphor is usually a multicrystallite material. Addition of this phosphor to an aqueous medium results in etching of the material along grain boundaries, leading to a decrease in particle size with time. This decrease in particle size causes two problems. The accompanying increase in powder surface area increases the rate of dissolution of the phosphor at any pH. In addition, the breakdown of the red phosphor particles into smaller particle size material widens the difference in particle size between the red and green phosphors in the triphosphor suspension, since the green component does not suffer this degradation. The difference in particle sizes of the red and green phosphor components of the triphosphor blend results in separation of the components along the length of the lamp envelope during the coating process causing visually detectable color variation along the length of the lamp during lamp operation.

Figure 2:
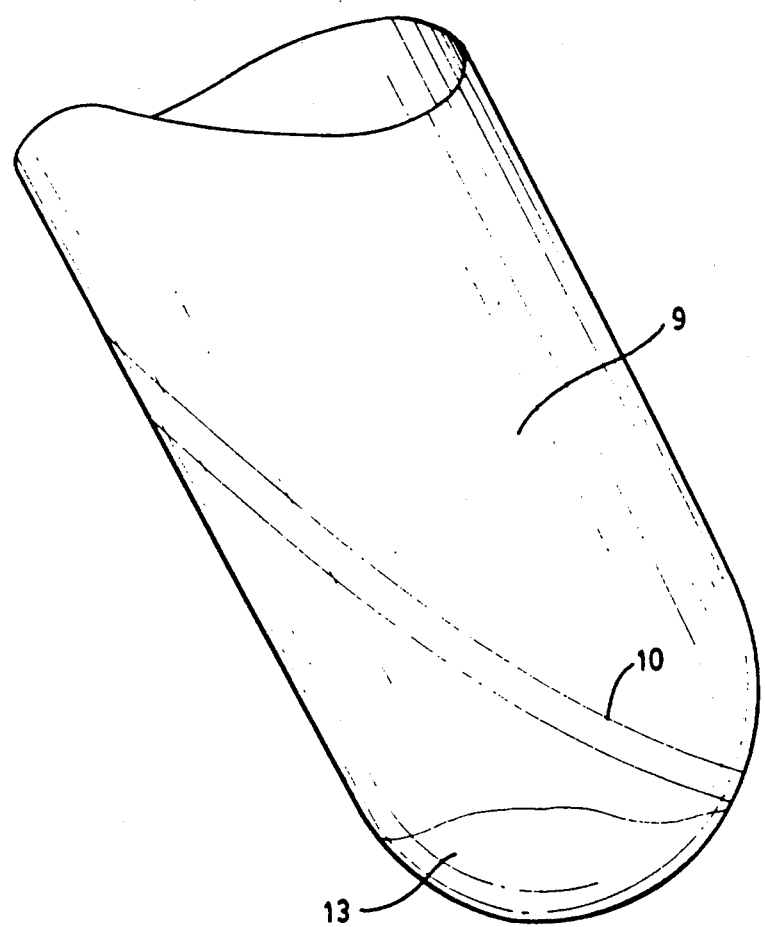
FIG. 2 illustrates the various phases of a sample of a coating suspension including $Y_2O_3$:Eu (without a protective coating) which has been centrifuged at 10,000 rpm for 30 minutes.

Experiments Involving Degraded Water Base Phosphor Suspensions Including $Y_2O_3$:Eu The following experiments were conducted on a degraded lot of a triphosphor suspension which needed an additional 51% red phosphor (% by mass of total initial phosphor) to bring the suspension to color specifications. A sample of the suspension was centrifuged at 10,000 rpm for 30 minutes. FIG. 2 schematically shows the breakdown of the suspension sample after centrifugation. The centrifigation gave rise to an upper liquid phase 9 at the bottom of which was a thin mocha colored solids layer 10 below which lay a white solids mass 13, the phosphor. The intermediate layer of thin colored solids 10 is referred to herein as the "scum layer." The breakdown shown in FIG. 2 was observed under 253.7 nm radiation. The scum layer does not display any fluorescence under 254 nm or 365 nm radiation.

The scum material was dried and its thermal decomposition studied. The major weight loss occurs by about 300° C. and is about 76.2% of the initial mass. The scum has a long thermal tail, losing an additional 3% of initial mass over the next 700° which puts the temperature well beyond the range of most lamp lehring furnaces. This leads to the lamp lehring problem referred to above.

The dried material gave no diffraction pattern indicating that the scum layer is amorphous as formed, but X-ray diffraction conducted after heating at about 1000° C. for 20 minutes in air confirmed the presence of yttrium. A sample of the scum was ignited to 800° C., resulting in a white, dense solid which was weighed and analyzed for yttrium. About 38% of the material is yttrium oxide.

The scum layer was found to include hydroxo compounds of yttrium, aluminum, and europium, Polyox fragments and metal-organic complexes. The reaction kinetics and endothermicity of the constituents of the scum layer lead to the lehring problems mentioned earlier.

Decrease In Particle Size Red Phosphor In Aqueous Medium

Dissolution of the red phosphor and multicrystallite breakup leads to a reduction in particle size of the phosphor.

A dispersion of GTE phosphor 2345 Lot YCX681 was made in deionized water, the phosphor concentration being 20 wt% of the suspension. Initial pH of the deionized water was 5.3. The sample was held over for 2400 hours, after which particle size measurements were made on a Malvern 3600Ec laser diffraction system. Ultrasound was used at the 100% level for 15 minutes before particle size measurement, and at the 70% level during measurement of the same. Three independent runs were made on the Malvern apparatus. A control sample of the phosphor which did not undergo any water-base holdover was also measured in the same manner. Table I shows the effect of water base holdover on the particle size of the red phosphor. The decrease in particle size of the phosphor at every single volume % (90, 50, and 10) is clearly evident. The 90% size decreased from 11.3 microns to 7.67 microns, the 50% size reduced from 5.1 microns to 3.6 microns and the 10% size changed from 0.94 to 0.67 microns. A decrease in particle size should be accompanied by an increase in the specific surface area. This is also evident in Table I, in an increase from 2.98 m²/cc for the no holdover sample to 3.83 m²/cc for the water base holdover phosphor.

TABLE I

| EFFECT OF HOLDOVER ON 2345 PSD | | |
|---|---|---|
| A | | |
| D(v,0.5) = 5.10 μg | D(v,0.5) = 5.13 μg | D(v,0.5) = 5.00 μg |
| D(v,0.9) = 11.29 μg | D(v,0.9) = 11.44 μg | D(v,0.9) = 11.14 μg |
| D(v,0.1) = 0.94 μg | D(v,0.1) = 0.95 μg | D(v,0.1) = 0.92 μg |
| D(4,3) = 5.66 μg | D(4,3) = 5.71 μg | D(4,3) = 5.60 μg |
| D(3,2) = 2.55 μg | D(3,2) = 2.57 μg | D(3,2) = 2.53 μg |
| Span = 2.0 | Span = 2.0 | Span = 2.0 |
| Spec. surf. area 2.9852 sq.s./cc. | Spec. surf. area 2.9657 sq.s./cc. | Spec. surf. area 3.0115 sq.s./cc. |
| B | | |
| D(v,0.5) = 3.66 μg | D(v,0.5) = 3.55 μg | D(v,0.5) = 3.59 μg |
| D(v,0.9) = 7.65 μg | D(v,0.9) = 7.50 μg | D(v,0.9) = 7.87 μg |
| D(v,0.1) = 0.69 μg | D(v,0.1) = 0.66 μg | D(v,0.1) = 0.67 μg |
| D(4,3) = 3.93 μg | D(4,3) = 3.82 μg | D(4,3) = 3.94 μg |
| D(3,2 = 1.92 μg | D(3,2) = 1.86 μg | D(3,2) = 1.88 μg |
| Span = 1.9 | Span = 1.9 | Span = 2.0 |
| Spec. surf. area 3.7832 sq.s./cc. | Spec. surf. area 3.8829 sq.s./cc. | Spec. surf. area 3.8410 sq.s./cc. |

A - No Holdover
B - 20 wt % Phosphor; 2400 Hour Holdover
Phosphor used: Type 2345, Lot-YCX 681

Solubility of the Red Phosphor: A Thermodynamic Study

The conversion of yttrium oxide, in the presence of water, to yttrium hydroxide, is characterized by a negative $\Delta G$ of reaction. It is, therefore, appropriate to investigate the thermodynamics of yttrium hydroxide solubility in order to study the solubility of the red phosphor.

The following equilibria are considered between yttrium hydroxide in the solid phase, denoted by $Y(OH)_3(s)$, and seven different yttrium ions in solution. Of these seven ions, five are mononuclear and the balance are polynuclear in yttrium.

MONONUCLEAR COMPLEXES OF YTTRIUM

1. $Y(OH)_{3(s)} = Y^{3+} + 3OH^-$
   $K_s = [Y^{3+}][OH^-]^3$
2. $Y(OH)_{3(s)} = Y(OH)^{2+} + 2OH^-$
   $K_{s11} = K_s\beta_{11} = [Y(OH)^{2+}][OH^-]^2$
3. $Y(OH)_{3(s)} = Y(OH)_2^+ + OH^-$
   $K_{s21} = K_s\beta_{21} = [Y(OH)_2^+][OH^-]$
4. $Y(OH)_{3(s)} = Y(OH)_{3(soln)}$
   $K_{s31} = K_s\beta_{31} = [Y(OH)_3]$
5. $Y(OH)_{3(s)} + OH^- = Y(OH)_4^-$
   $K_{s41} = K_s\beta_{41} = [Y(OH)_4^-]/[OH^-]$

POLYNUCLEAR COMPLEXES OF YTTRIUM

6. $2Y(OH)_{3(s)} = Y_2(OH)_2^{4+} + 4OH^-$
   $K_{s22} = K_s^2\beta_{22} = [Y_2(OH)_2^{4+}][OH^-]^4$
7. $3Y(OH)_{3(s)} = Y_3(OH)_5^{4+} + 4OH^-$
   $K_{s53} = K_s^3\beta_{53} = [Y_3(OH)_5^{4+}][OH^-]^4$ In the above reactions $K_s$ is the solubility product for $Y(OH)_3$ and $\beta_{ba}$ is the stability constant for the complex $M_aA_b$. The complex formation of the species $M_mA_n$ may be represented by the general equation (Kotrly and Sucha, Handbook of Chemical Equilibria in Analytical Chemistry, Ellis Horwood, 1985):

$$a/m \, M_mA_{n(s)} = M_aA_{b(soln)} + (an/m - b)A$$

where $K_{sba} = \beta_{ba}K_s^{a/m}$

It follows that for reaction 6, $m=1$, $n=3$, $a=2$ $b=2$, $M=Y$ and $A=OH$.

Similarly, for reaction 7, $m=1$, $n=3$, $a=3$ and $b=5$.

The stability constants $\beta_{ba}$ are defined as follows:

$\beta_{11} = [Y(OH)^{2+}]/[Y^{3+}][OH^-]$ $\beta_{21} = [Y(OH)_2^+]/[Y^{3+}][OH^-]^2$ $\beta_{31} = [Y(OH)^3]/[Y^{3+}][OH^-]^3$ $\beta_{41} = [Y(OH)_4^-]/[Y^{3+}][OH^-]^4$ $\beta_{22} = [Y_2(OH)^{24+}]/[Y^{3+}]^2[OH^-]^2$ $\beta_{53} = [Y_3(OH)_5^{4+}]/[Y^{3+}]^3[OH^-]^5$ The values for $\log \beta$ are obtained from Kotrly and Sucha as:
$\beta_{11} = 6.3$, $\beta_{21} = 11.6$, $\beta_{31} = 16.0$, $\beta_{41} = 19.5$, $\beta_{22} = 13.8$ and $\beta_{53} = 38.4$.

The solubility product for $Y(OH)_3$ is given in the same reference as, $pK_s = 23.2$.

The following thermodynamic equations, which describe the solubility of the various yttrium ions as a function of pH, can be derived from the above information:

$\log[Y^{3+}] = 18.8 - 3\,pH$     1

$\log[Y(OH)^{2+}] = 11.1 - 2\,pH$     2

$\log[Y(OH)_2^+] = 2.4 - pH$     3

$\log[Y(OH)_3] = -7.2$     4

$\log[Y(OH)_4^-] = pH - 17.7$     5

$\log[Y_2(OH)_2^{4+}] = 23.4 - 4\,pH$     6

$\log[Y_3(OH)_5^{4+}] = 24.8 - 4\,pH$     7

Figure 3:
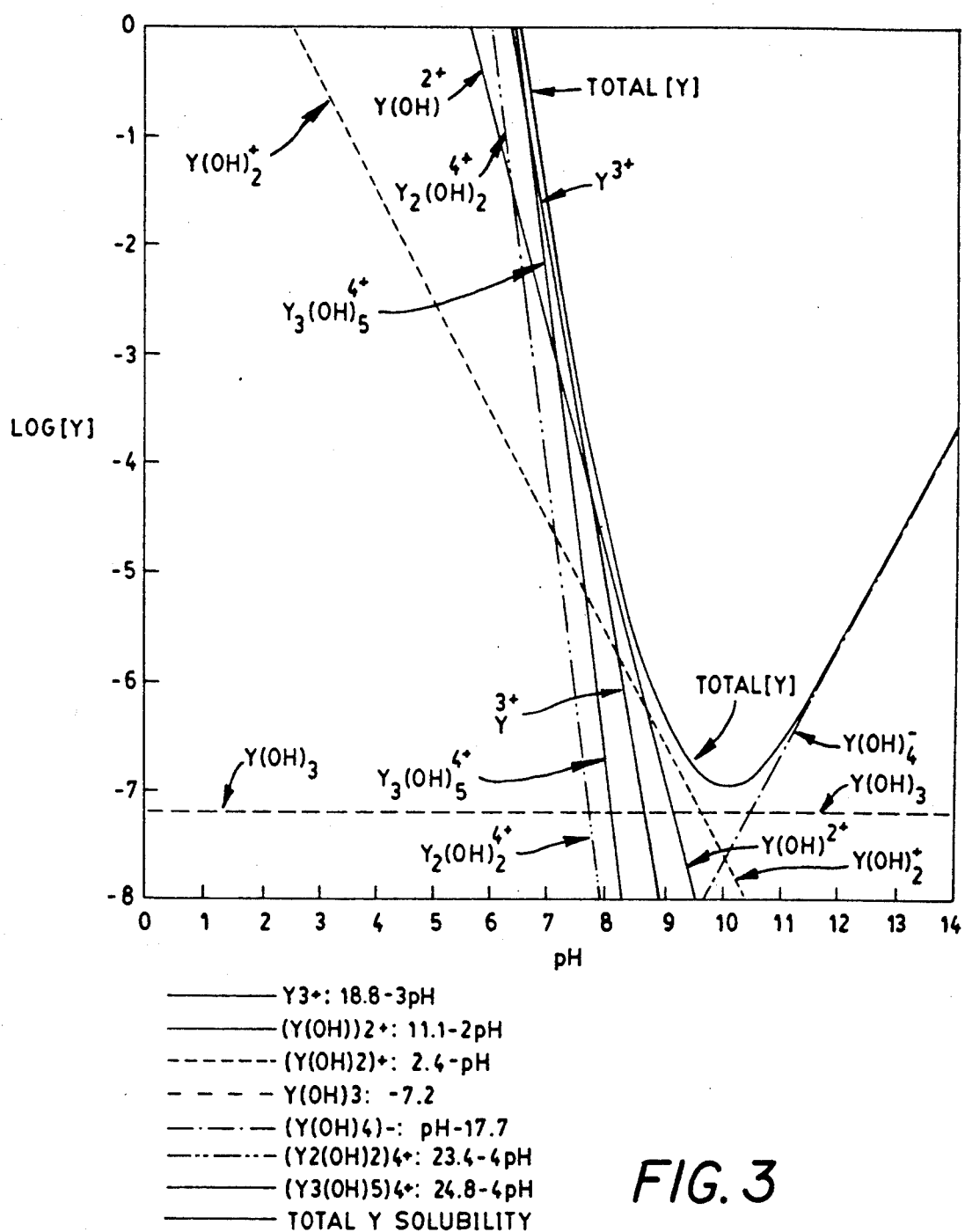
FIG. 3 graphically illustrates the solubility of yttrium hydroxide in water at 25° C. and ionic strength of zero.

A graphic representation of the solubilities of these seven species is shown in FIG. 3. The ordinate of the graph is $\log[Y]$, and the concentrations of the polynuclear species are multiplied by the appropriate factors to reflect this. For example, one mole of $Y_2(OH)_2^{4+}$ contains two moles of Y. The multiplication factor to obtain [Y] for this species is, therefore, 2. FIG. 3 also shows the total solubility of Y, computed from a summation of the seven species, solubilities. A minimum in the Y solubility is predicted at a pH of about 10.

Figure 4:
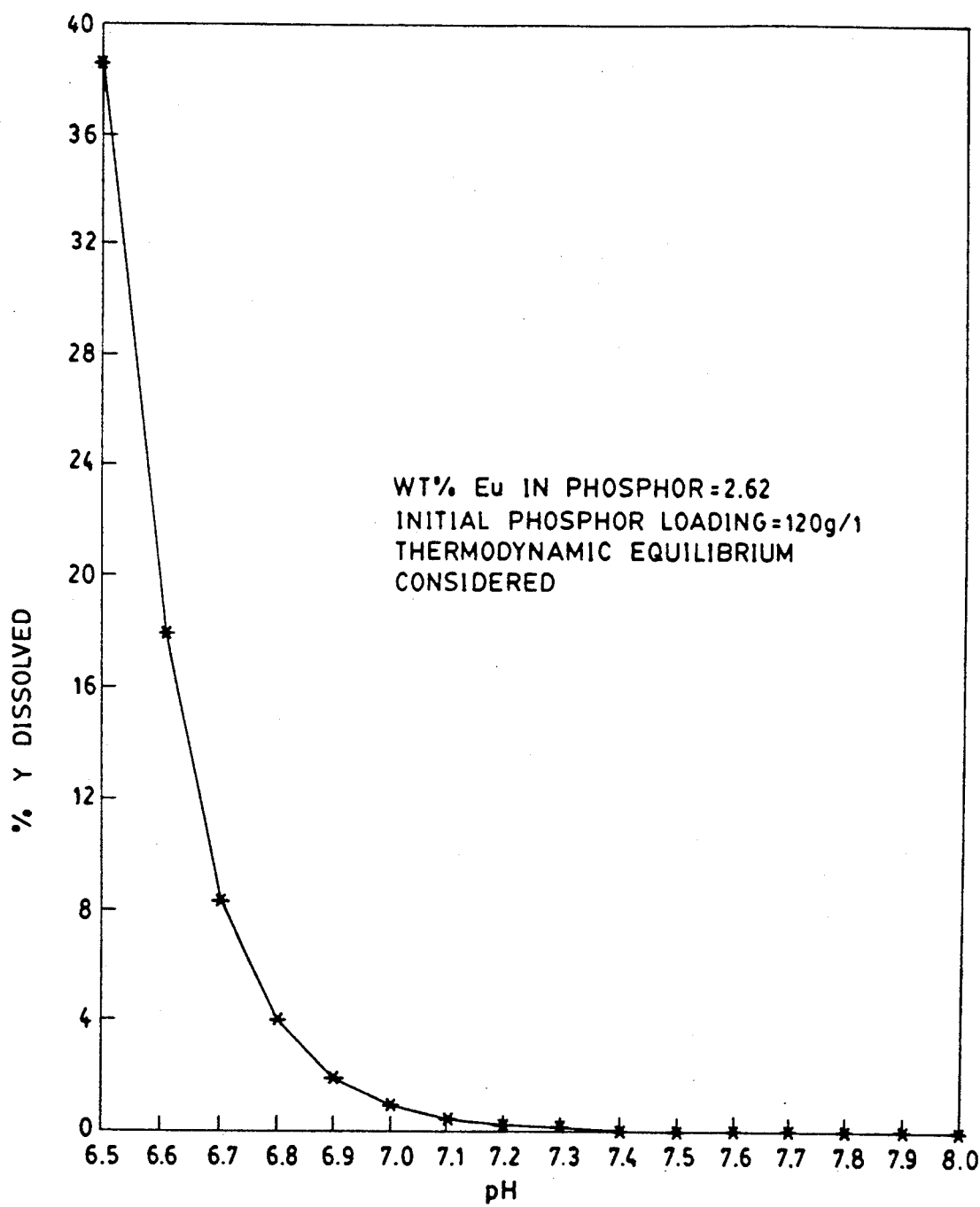
FIG. 4 graphically illustrates the effect of pH on dissolution of $Y_2O_3$:Eu phosphor in water at 25° C.

Results from this study were used to predict the effect of pH on the dissolution of the red phosphor, $Y_2O_3$:Eu. A typical red phosphor containing 2.62 weight percent Eu was considered. A standard concentration of 120 grams of this red phosphor per liter of water was studied. FIG. 4 quantifies the adverse effects of low pH on the solubility of this phosphor. If the pH drops from the basic side to about 6.5, for example, almost 39% of the yttrium in the phosphor will have dissolved. The drop in pH can easily be brought about by the need to add ALON C whose acidic nature has been discussed earlier. It also follows that a significant amount of the dissolved Y will precipitate out on the surface of the phosphor particles when the suspension pH subsequently increases.

This rise in pH is due to the basic nature of the yttrium oxide phosphor. This rise, dictated by thermodynamics, stems from the necessary condition that an ionic charge balance should exist between all soluble species at equilibrium.

The thermodynamic stable pH for the ALON C/$Y_2O_3$:Eu containing phosphor system was studied. The stable pH may be approximated by the pH of an aqueous solution saturated with respect to aluminum hydroxide and yttrium hydroxide, and is the equilibrium pH which would result from the addition of ALON C and yttrium oxide to pure water. It can be shown that the solution of the following nonlinear equation will yield the stable pH for this system:

$$3*10^{**}(18.8 - 3x) + 2*10^{}(4.68 - 2x) + 10^{}(2.4 - x) +$$
$$4*10^{**}(23.4 - 4x) + 4*10^{**}(24.8 - 4x) +$$
$$3*10^{**}(9.66 - 3x) + 2*10^{}(4.68 - 2x) + 10^{}(0.36 - x) +$$
$$4*10^{**}(11.62 - 4x) + 5*10^{}(15.08 - 5x) + 10^{}(-x) =$$
$$10^{}(x - 17.7) + 10^{}(x - 13.34) + 10^{**}(x - 14)$$

1

The left hand side of equation 1 is the summation of the product of the concentration and valence of all positive ions in solution: the five yttrium species, the five aluminum species, and the hydrogen ion. The right hand side is the summation of the product of the concentration and valence of all negative ions in solution: one yttrium species, one aluminum species, and the hydroxyl ion. The equation was solved on the Compaq 386/20 using the Newton Raphson algorithm. The stable pH is 8.285.

Incorporating the effects of deionized water (the pH of which is less than 7) in this calculation is accomplished by calculating the nonhydroxyl anion from the pH value and entering it in the fourth term on the right hand side of equation 1. The effect of an acidic deionized water will be to decrease the value of stable pH. The magnitude of this drop is small. As an example, use of deionized water of pH 5 instead of pure water at pH 7 drops the stable pH from 8.285 to 8.177.

The europium activator of the yttrium oxide phosphor can also dissolve in the aqueous medium. Thus, a detailed ionic balance needs to contain europium ions also. The $Eu^{3+}$ species was incorporated in the left side of equation 1. This results in a very small increase in the value of the stable pH from 8.285 to 8.31.

It is concluded, therefore, that the pH of the water used for making lamp suspensions and the presence of europium in the solution have only a secondary influence on the value of the stable pH for this system.

Although the stable pH of the suspension is about 8.3, it has been found that the pH of the system should be between 9 and 9.5, inclusive.

This pH level is attained, where the pH of the suspension is less than 9, by ammoniating the suspension to achieve a pH of 9 to 9.5.

The ammoniating species can be ammonium hydroxide ($NH_4OH$), or one or more member of of the amine family of organic compounds, such as triethyl amine —$(C_2H_5)_3N$; diethyl amine —$(C_2H_5)_2NH$; iso-butyl amine —$(CH_3)_2CHCH_2NH_2$.

Where the pH of the suspension is greater than 9.5, the pH is adjusted to be with the range from 9 to 9.5 by adding a weak organic acid) to the suspension. Examples of acids suitable for accomplishing this pH adjustment include acetic acid —$CH_3COOH$; and oxalic acid ($HO_2CCO_2H$).

By maintaining the pH of the water base coating suspension including alumina, e.g., ALON C, and europium-doped yttrium oxide between 9 and 9.5, the solubility of the phosphor is negligible and the solubility of aluminum from the alumina is at an acceptable level for the necessary binding action it performs in the coating.

Prior to this invention, the pH of water base triphosphor suspensions at one of GTE Product Corporation's fluorescent lamp manufacturing facilities was found to vary significantly, ranging from an acidic 6.5 to a basic 10. Table II lists the results of measurements made on 27 different tanks at the facility.

TABLE II

| Tank # | Blend Type | pH |
|---|---|---|
| 12 | tri-white | 6.78 |
| 25 | tri-white | 8.46 |
| 36 | tri-white | 9.65 |
| 53 | tri-white | 10.01 |
| 57 | tri-white | 9.21 |
| 82 | tri-white | 8.86 |
| 2 | tri-lwx | 8.29 |
| 29 | tri-lwx | 8.28 |
| 35 | tri-lwx | 7.31 |
| 47 | tri-lwx | 8.60 |
| 59 | tri-lwx | 8.36 |

TABLE II-continued

| Tank # | Blend Type | pH |
|---|---|---|
| 103 | lite white | 6.50 |
| 4 | soft brite | 6.66 |
| 27 | soft brite | 7.31 |
| 75 | soft brite | 10.16 |
| 93 | soft brite | 8.71 |
| 102 | soft brite | 9.32 |
| 114 | soft brite | 10.05 |
| 91 | royal white | 9.29 |
| 11 | 3K | 9.29 |
| 32 | 3K | 7.89 |
| 74 | 3K | 9.58 |
| 40 | red/blue | 8.11 |
| 65 | red/blue | 7.87 |
| 72 | red/blue | 9.78 |
| 90 | red/blue | 7.90 |

Each of the water base suspensions of the phosphor blend types identified in the foregoing table included ALON C. Tri-white phosphor includes $Y_2O_3$:Eu phosphor, cerium terbium magnesium aluminate:cerium:terbium phosphor (e.g., GTE Type 2297); and barium magnesium aluminate:europium phosphor (e.g., GTE Type 2461). Lite white phosphor blend includes $Y_2O_3$:Eu phosphor (GTE Type 2345), cerium terbium magnesium aluminate:cerium:terbium phosphor (e.g., GTE Type 2297); and barium magnesium aluminate:europium phosphor (e.g., GTE Type 2461). Soft brite phosphor blend includes $Y_2O_3$:Eu phosphor (GTE Type 2345), cerium terbium magnesium aluminate:cerium:terbium phosphor (e.g., GTE Type 2297); and barium magnesium aluminate:europium phosphor (e.g., GTE Type 2461). Royal white phosphor blend includes $Y_2O_3$:Eu phosphor (GTE Type 2345), cerium terbium magnesium aluminate:.cerium:terbium phosphor (e.g., GTE Type 2297); and barium magnesium aluminate: europium phosphor (e.g., GTE Type 2461). Three (3)K phosphor blend includes $Y_2O_3$:Eu phosphor (GTE Type 2345), cerium terbium magnesium aluminate:cerium:terbium phosphor (e.g., GTE Type 2297); and barium magnesium aluminate: europium phosphor (e.g., GTE Type 2461). Red/blue blend includes $Y_2O_3$:Eu phosphor (GTE Type 2345), $BaMg_2Al_{16}O_{27}$:Eu (GTE Type 2461).

Since January 1990, when the pH of the water base triphosphor coating suspensions at this same facility were first adjusted to and maintained at from 9 to 9.5, in accordance with this invention, there have been virtually no hold over problems.

While there have been shown and described what at present are considered preferred embodiments of the invention, it will be apparent to those skilled in the art that various changes and modifications may be made herein without departing from the scope of the invention as defined by the appended claims.

What is claimed is:

1. A method of determining whether an europium doped yttrium oxide red phosphor has become degraded in a water base phosphor coating suspension, the method comprising: (a) centrifuging said suspension, (b) separating an aqueous portion from a solids portion, (c) exposing a surface portion of said solids to UV radiation at 254 nm or 365 nm, (d) observing the presence or absence of fluorescence from said top layer of solids wherein the absence of fluorescence is indicative of a degraded phosphor.

* * * * *